(12) United States Patent
Moody et al.

(10) Patent No.: US 6,790,170 B2
(45) Date of Patent: Sep. 14, 2004

(54) RADIOACTIVE SOURCE WIRE AND DUAL LUMEN CATHETER SYSTEM FOR BRACHYTHERAPY

(75) Inventors: Michael R. Moody, Buford, GA (US); Anthony D. Coon, Suwane, GA (US); Richard A. Brauckman, Cumming, GA (US); Jack C. White, Alpharetta, GA (US)

(73) Assignee: Theragenics Corporation, Buford, GA (US)

( * ) Notice: Subject to any disclaimer, the term of this patent is extended or adjusted under 35 U.S.C. 154(b) by 94 days.

(21) Appl. No.: 10/010,250

(22) Filed: Nov. 7, 2001

(65) Prior Publication Data

US 2002/0147379 A1 Oct. 10, 2002

Related U.S. Application Data

(60) Provisional application No. 60/247,026, filed on Nov. 8, 2000, and provisional application No. 60/306,674, filed on Jul. 20, 2001.

(51) Int. Cl.[7] ............................................. A61M 36/12
(52) U.S. Cl. ........................................................... 600/3
(58) Field of Search ....................................... 600/1–8

(56) References Cited

U.S. PATENT DOCUMENTS

| | | | |
|---|---|---|---|
| 5,199,939 A | 4/1993 | Dake et al. ..................... 600/3 |
| 5,282,781 A | 2/1994 | Liprie ............................ 600/3 |
| 5,354,257 A | * 10/1994 | Roubin et al. ................. 600/7 |
| 5,395,300 A | 3/1995 | Liprie ............................ 600/3 |
| 5,503,613 A | 4/1996 | Weinberger ................... 600/3 |
| 5,503,614 A | 4/1996 | Liprie ............................ 600/7 |
| 5,540,659 A | 7/1996 | Teirstein ...................... 604/104 |
| 5,556,389 A | 9/1996 | Liprie ........................ 604/264 |
| 5,575,749 A | 11/1996 | Liprie ............................ 600/3 |
| 5,618,266 A | 4/1997 | Liprie ........................... 604/21 |
| 5,624,372 A | 4/1997 | Liprie ............................ 600/3 |
| 5,807,231 A | 9/1998 | Liprie ............................ 600/3 |
| 5,833,593 A | 11/1998 | Liprie ............................ 600/3 |
| 5,840,064 A | 11/1998 | Liprie ........................... 604/96 |
| 5,857,956 A | 1/1999 | Liprie ............................ 600/7 |
| 5,899,882 A | 5/1999 | Waksman et al. ............. 604/95 |
| 5,924,974 A | 7/1999 | Löffler ........................... 600/3 |
| 6,024,690 A | 2/2000 | Lee et al. ...................... 600/3 |
| RE36,628 E | 3/2000 | Sagae et al. ................ 148/537 |
| 6,056,686 A | 5/2000 | Mawad .......................... 600/3 |
| 6,059,713 A | 5/2000 | Urick et al. ................... 600/3 |
| 6,080,160 A | 6/2000 | Chen et al. ................... 606/72 |

OTHER PUBLICATIONS

Nath et al., "Intravascular Brachytherapy Physics", *Medical Physics*, vol. 26, No. 2, Feb. 1999, pp. 120–152.

* cited by examiner

*Primary Examiner*—Samuel G. Gilbert
(74) *Attorney, Agent, or Firm*—Knoble Yoshida & Dunleavy LLC

(57) ABSTRACT

A dual lumen catheter system for the positioning of a radioactive material for therapeutic radiation treatment of the body is disclosed. The dual lumen catheter includes a guidewire lumen and a blind lumen provided for introduction of a radiation source wire. The dual lumen catheter provides the advantage that the radiation source wire does not contact body tissue thereby eliminating the need for sterilization of the wire for reuse. Also disclosed are a radiation source wire having a tapered distal end of the wire core such that radioactive material and other components of the source wire can be applied to the outer surface thereof without exceeding a predetermined maximum outside diameter. Also disclosed is a source train cask for use with the catheter system and radiation source wire of the invention. The source train cask permits convenient handling and feeding of the radiation source wire without exposure of the medical personnel to radiation.

21 Claims, 8 Drawing Sheets

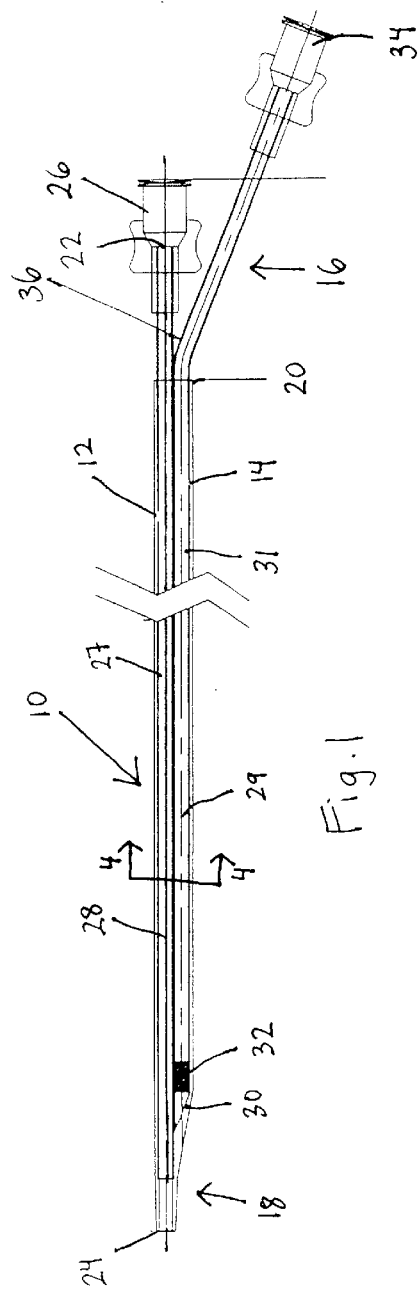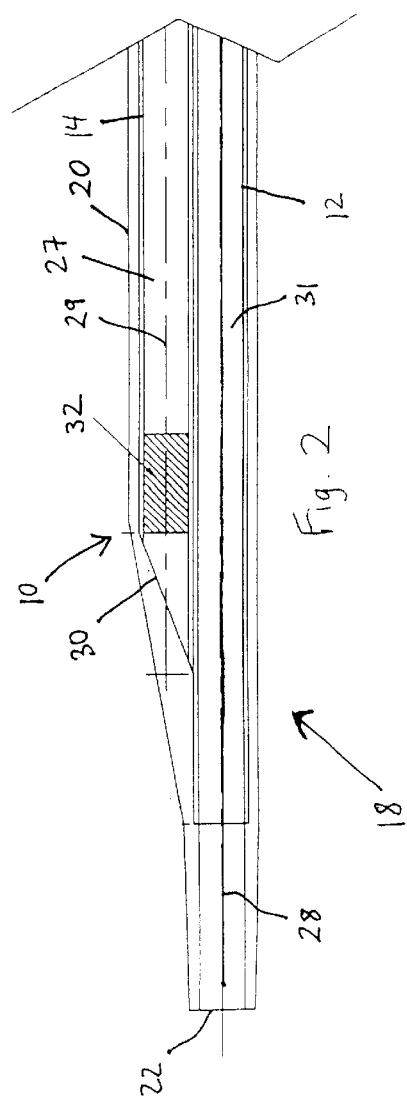

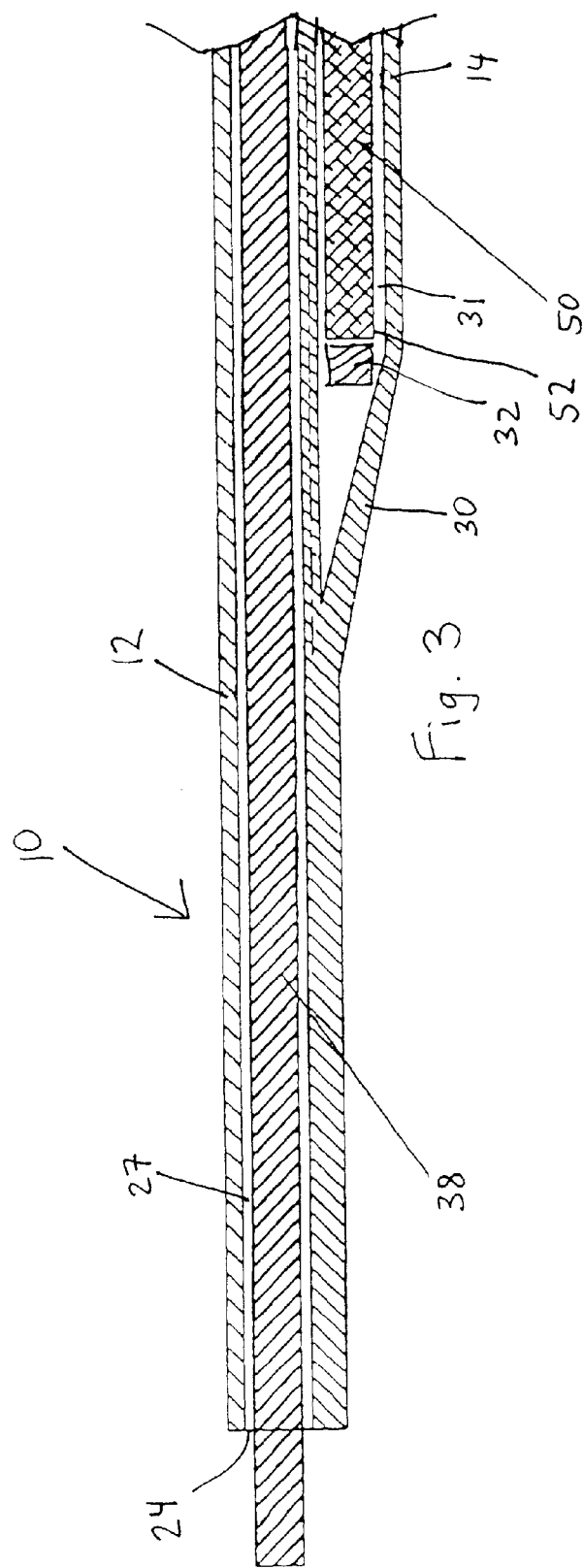

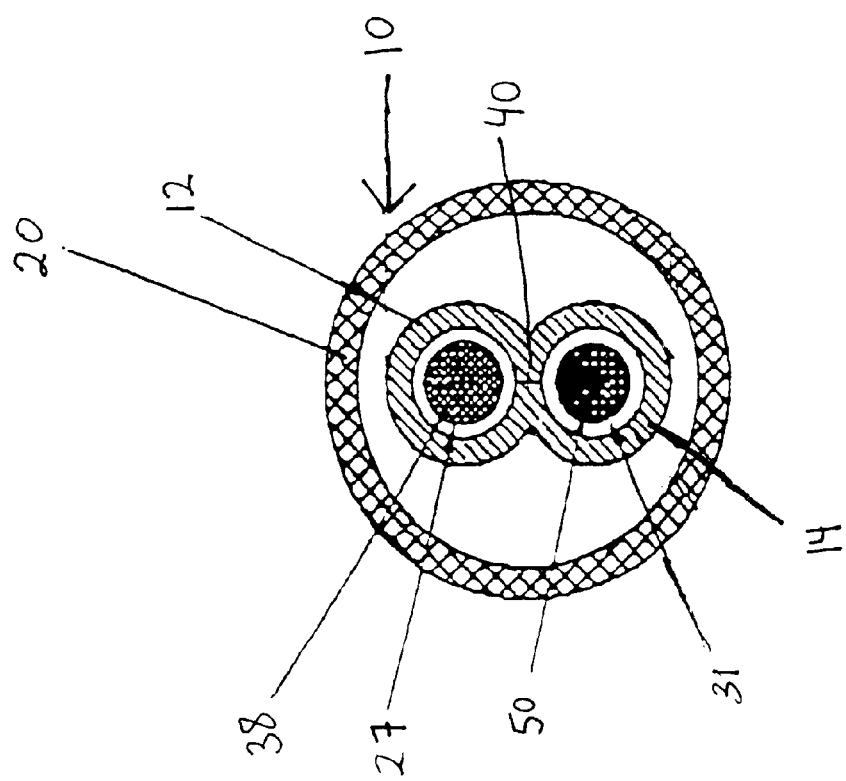

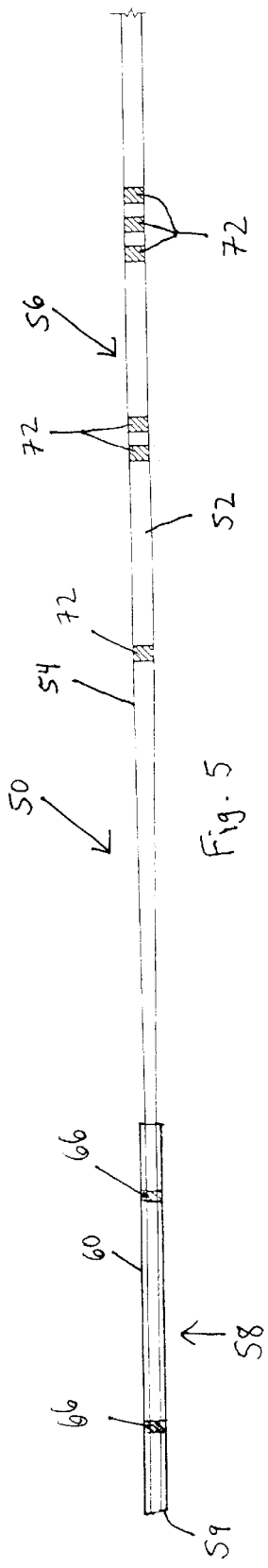

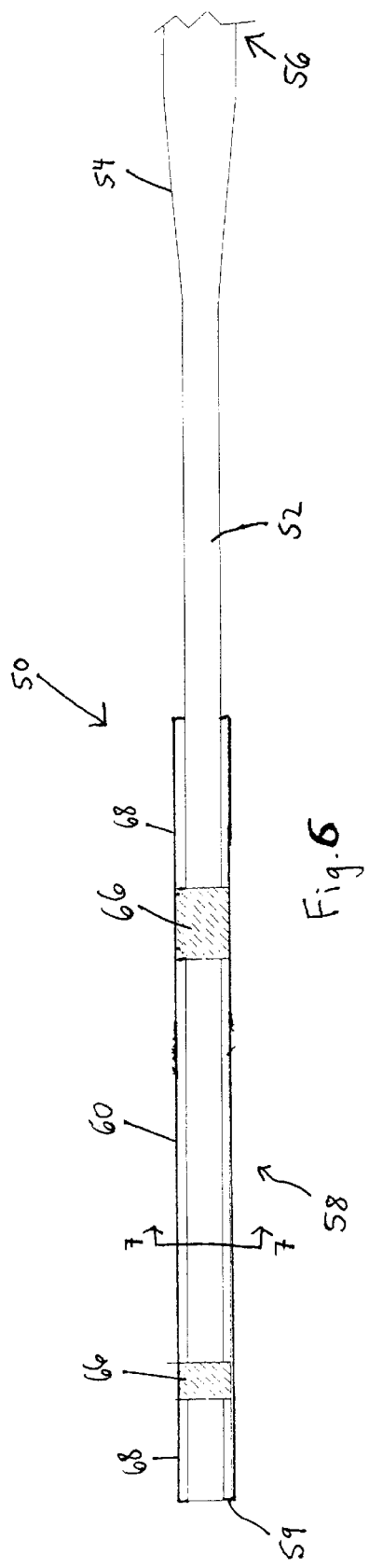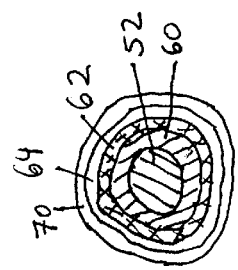
Fig. 6
Fig. 7

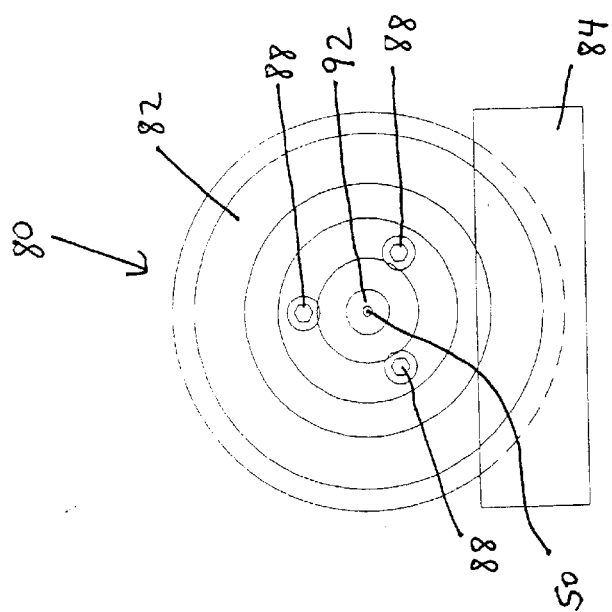
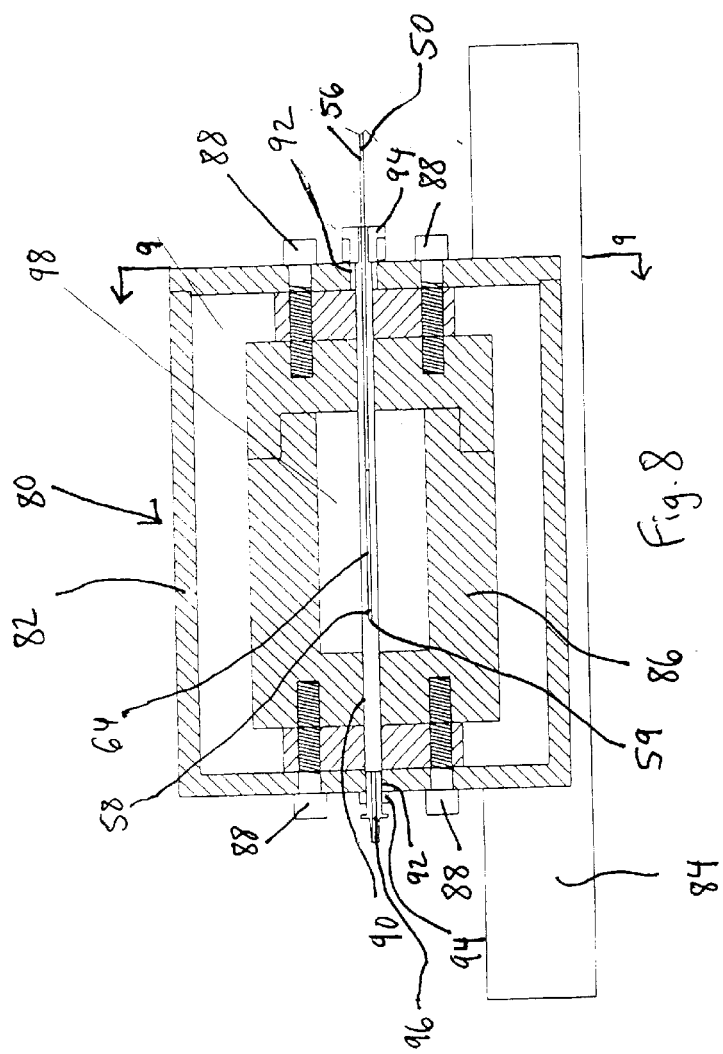

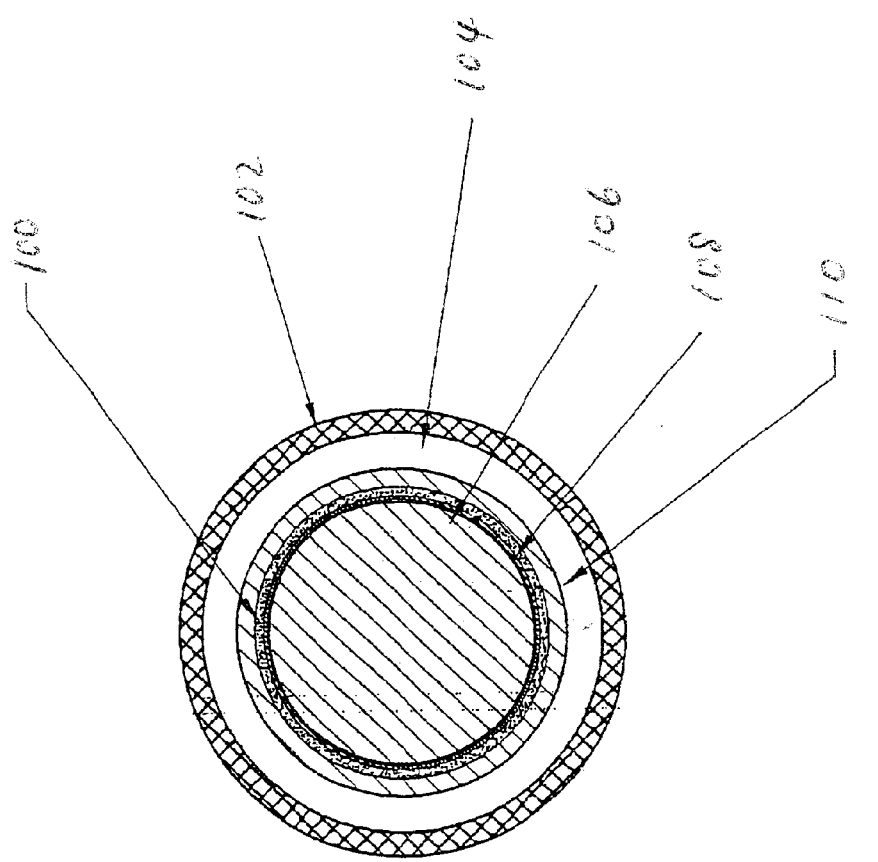

RADIOACTIVE SOURCE WIRE AND DUAL LUMEN CATHETER SYSTEM FOR BRACHYTHERAPY

RELATED APPLICATION DATA

This application claims the benefit of U.S. provisional patent application No. 60/247,026, filed on Nov. 8, 2000, pursuant to 35 U.S.C. §119(e), and the benefit of U.S. provisional patent application No. 60/306,674, filed on Jul. 20, 2001, pursuant to 35 U.S.C. §119(e).

FIELD OF THE INVENTION

The present invention relates to a radioactive source wire and a dual lumen catheter system for positioning a radioactive material in the body for brachytherapy. More particularly, the invention relates to a radioactive source wire and dual lumen catheter system for positioning a radioactive material at a desired site in the body without direct contact between the radioactive source and body tissue.

BACKGROUND OF THE INVENTION

The body's healing response to wounds includes the formation of scar tissue. This response occurs in the vascular system after injury or trauma such as may be caused by angioplasty or other similar treatments thereby resulting in a condition commonly referred to as restenosis. As a result of restenosis, scar tissue grows on the inner walls of the vessels vascular system thereby causing an undesirable narrowing of the vessels. Accordingly, it is desirable to prevent or inhibit restenosis as part of the overall treatment of the vascular system following procedures such as angioplasty or the like. While angioplasty currently has a short-term success rate of 90–95%, due to restenosis, about 30–50% of patients' vessels narrow to approximately 50% or less of the size of the native vessel.

A variety of different therapies for the prevention of restenosis have been employed including light therapies, chemotherapeutic agents, stents, atherectomy devices and lasers. One method for preventing or inhibiting restenosis that has shown promise is the irradiation of the inner vascular wall subsequent to angioplasty in order to prevent or inhibit scar tissue formation sometimes referred to as intimal hyperplasia. However, the devices for delivery of radiation sources to the treatment site suffer from a number of drawbacks that limit their usefulness and effectiveness.

U.S. Pat. No. 5,503,614 (Liprie) relates to a flexible source wire for radiation treatment of diseases. The source wire includes a radioactive source and may be maneuvered to the site of treatment via various vessels in the body. The flexible source wire includes a flexible housing formed by an elongate, hollow tube such as Nitinol® or a titanium/nickel alloy which exhibits little or no memory retention when bent. The disclosed device also includes an internal flexible backbone wire for placement within the hollow tube and which may be constructed from the same material as the hollow tube.

U.S. Pat. No. 5,833,593 (Liprie) relates to a flexible source wire for localized internal radiation of tissue which is capable of maneuvering through tortuous narrow body vessels. The source wire is provided with an elongate, flexible housing tube having one end modified to receive a radioactive core. The source wire may be constructed from nickel/titanium alloys. Both ends of the source wire are sealed and the end containing the radioactive material is rounded to ease navigation of body vessels.

U.S. Pat. No. 5,084,002 (Liprie) relates to an ultra-thin, high dose iridium source for remote treatrrfent of cancerous tissue with radiation. This device is specifically designed for use in areas of the human body where minimization of trauma to adjacent tissue is a high priority. As a result, the radioactive source is encapsulated in a thin platinum delivery wire with an ultra-thin cross section. A similar device is also disclosed in U.S. Pat. No. 5,141,487 (Liprie).

U.S. Pat. No. 5,302,168 (Hess) relates to a method and apparatus for restenosis treatment after angioplasty by application of a radioactive dose to the reduced region of the artery. In one embodiment disclosed in this patent, a radioactive dose is positioned in a housing located at the distal end of a catheter delivery device. The housing is provided with a window cutout covered by a sheath. The sheath is drawn back when the radioactive dose is positioned for treatment. A second embodiment disclosed in this patent involves attaching radioactive elements to an angioplasty balloon catheter and expanding the balloon in the area to be treated to force the radioactive elements into contact with the area to be treated.

U.S. Pat. No. 5,213,561 (Weinstein et al.) discloses methods and devices for preventing restenosis after angioplasty. More specifically, various embodiments are disclosed wherein a radioactive source is mounted at the end of a guide wire, is delivered inside a tube provided with a guide wire in a balloon catheter or is coated on a balloon expandable stent. A retractable sheath is employed to enclose the radiation source until irradiation is desired at which point the sheath is retracted.

U.S. Pat. No. 5,199,939 (Dake) discloses a radioactive catheter and a method for using the catheter for preventing restenosis after angioplasty. The method includes employing an elongate, flexible catheter with a radioactive source located in its distal end to irradiate the treatment zone. The radioactive catheter employs a plurality of cylindrical radioactive pellets disposed among a plurality of cylindrical spacers as the radioactive source.

The foregoing catheter systems suffer from a number of drawbacks. For example, many of the devices include a number of elements located between the radiation source and the area to be treated which results in shielding which may reduce the effect of the radiation and/or cause an irregular distribution of the radiation dose. Other devices provide the radioactive source material in a plurality of discrete elements which inherently results in different levels of radiation dose being applied to different parts of the treated area. Still other devices require repeated feeding and removal of a guidewire to locate the radiation dose and remove the radiation dose thereby making the treatment awkward and time-consuming for medical personnel. Other drawbacks of specific devices exist as well.

SUMMARY OF THE INVENTION

It is an object of certain embodiments of the present invention to overcome one or more of the drawbacks of existing devices for providing a dose of radiation to a localized treatment area in the body.

It is a further object of certain embodiments of the present invention to provide an improved radioactive source suitable for navigating tortuous narrow body vessels in order to position the radioactive source in close proximity to the treatment area.

It is a further object of certain embodiments of the present invention to provide devices wherein shielding of the radiation is minimized or substantially eliminated.

It is a still further object of certain embodiments of the present invention to provide devices that deliver a substantially uniform radiation dose to the area to be treated.

It is a still further object of certain embodiments of the present invention to provide a dual lumen catheter system for delivery of a radioactive source to a treatment area without contact between the radioactive source and body tissue These and other objects are accomplished by various embodiments of the present invention, which relates, in one aspect, to a radioactive source wire having a tapered distal end with which a radioactive material is associated. The source wire of the present invention may be made as a single unit thereby greatly reducing the chance that a portion of the source wire can break off during use. Also, the tapered distal end of the source wire allows the application of additional useful elements to the radioactive source wire while still providing a source wire having a diameter within a predetermined size range.

The present invention also relates to a dual lumen catheter system for delivery of a radioactive source wire to a localized area to be treated. The radioactive source wire may be a source wire in accordance with the present invention. The dual lumen catheter system includes structure that allows insertion of the radioactive source wire into the body without direct contact between the radioactive source wire and body tissue. Various embodiments of the dual lumen catheter system of the present invention overcome some of the drawbacks of prior art devices.

BRIEF DESCRIPTION OF THE DRAWINGS

FIG. 1 is shows a dual lumen catheter in accordance with the present invention;

FIG. 2 is a view of the distal end of the dual lumen catheter of the present invention;

FIG. 3 is a cross-sectional view of the dual lumen catheter of the present invention showing the guidewire and radiation source positioned in the catheter;

FIG. 4 is a cross-sectional view of the dual lumen catheter of the present invention taken along line 4—4 of FIG. 1;

FIG. 5 shows one embodiment of a radiation source wire in accordance with the present invention;

FIG. 6 shows a more detailed view of the distal end of the radiation source wire shown in FIG. 5;

FIG. 7 is a cross-sectional view of the distal end of the radiation source wire along the line 7—7 of FIG. 6;

FIG. 8 is a cross-sectional view of a source train cask for storing and feeding a radiation source wire to the catheter system of the invention;

FIG. 9 is an end view of the source train cask along the lines 9—9 in FIG. 8.

FIG. 11 is a cross-sectional view of the embodiment of FIG. 10, taken along the line 11—11 of FIG. 10.

DETAILED DESCRIPTION OF THE PREFERRED EMBODIMENTS

Figure 10:
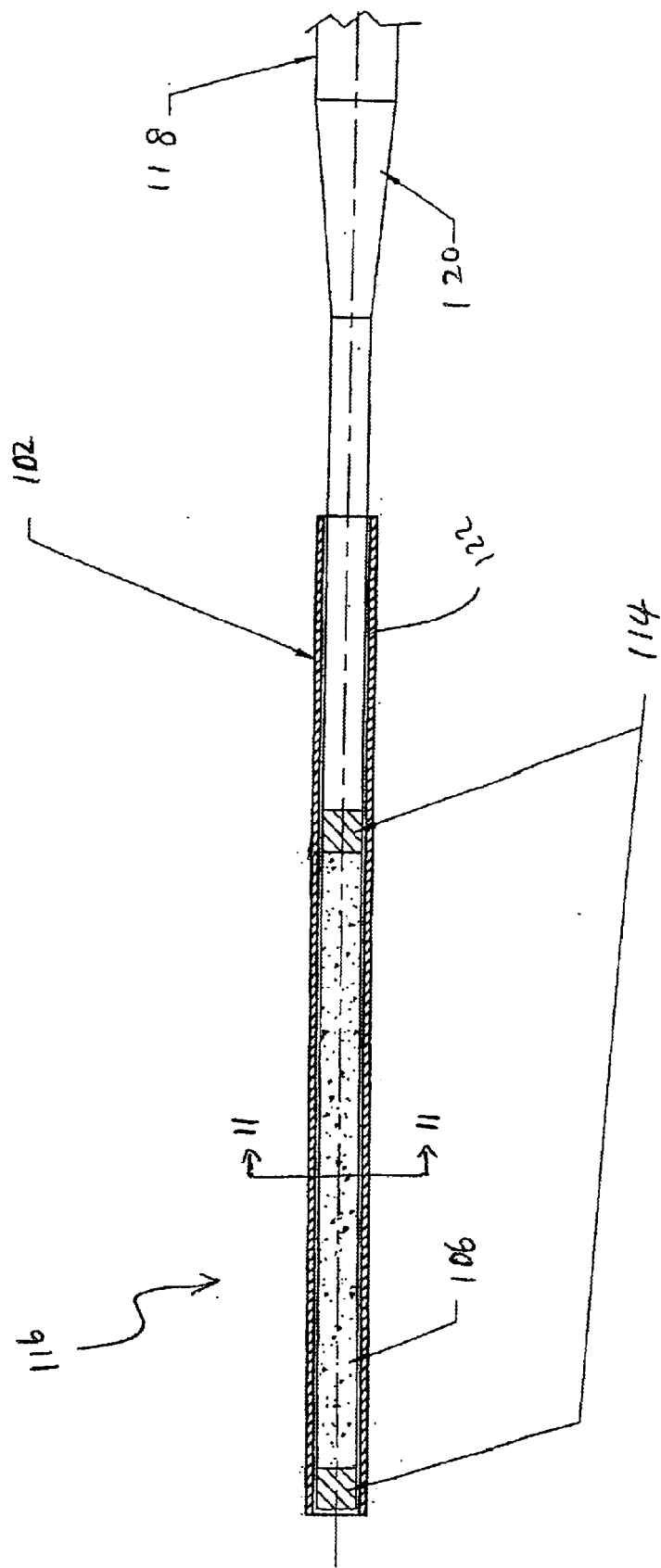
FIG. 10 is a cross-sectional view of another embodiment of the distal end of the radiation source wire of the present invention.

The present invention is directed to a catheter system and a radiation source wire for delivering a radioactive material to a desired treatment area in a body. The devices of the invention may be employed, for example, for reducing or preventing restenosis of a vessel in a body by irradiating the vessel. In addition, the devices of the present invention may also be employed for other treatments such as the repair or correction of the intraluminal lining or iliac or for femoral aneurysms; recanalization of injured vessels caused by blunt or penetrating trauma, recanalization of esophageal stenoses associated with carcinoma or benign structures, dilation of the aorta, dilation of biliary stenoses associated with strictures, tumors and cancer of the lungs, bronchial system, colon, brain, pancreas and common bile duct, and treatment of urethral strictures and tracheal strictures. Other treatments which require irradiation of tissue of the human or mammal body can also be carried out using the various embodiments of the apparatus and methods of the present invention.

The devices of the present invention can be employed to prevent the formation of scar tissue after trauma to the body in particular locations such as that which frequently results after angioplasty. By delivering radioactivity soon after the enlargement procedure, excessive growth of scar tissue can be inhibited. As a result, the incidence of repeated angioplastic interventions can be reduced.

In a first aspect, the present invention relates to a dual lumen catheter 10 shown in FIG. 1. The dual lumen catheter 10 includes a guidewire lumen 12 and a blind lumen 14. The dual lumen catheter 10 includes a proximal end 16 which is designed to remain outside the body and may be used for insertion of a guidewire 38, radiation source wire 50 and/or other treatment devices, and a distal end 18 which is designed to be inserted into the body and positioned at a desired location therein.

In the embodiment shown in FIG. 1, dual lumen catheter 10 is preferably formed from a suitable catheter material which is deformable to minimize trauma as the catheter 12 is inserted into the body through tortuous body vessels. Dual lumen catheter 10 may be used in combination with a conventional guide catheter 20 to avoid direct tissue contact with the dual lumen catheter 10. Such guide catheters 20 are known to persons skilled in the art and are preferably fabricated from polymeric materials. The cross-section of guide catheter 20 can be any suitable shape but is most preferably circular since there are then no edges which might cause trauma as the dual lumen catheter 10 is inserted and removed from the body.

Suitable catheter materials are known in the art. Preferred catheter materials can include polyethylene, polyimide, polyetheramide or other polyolefins. Other suitable materials may be employed as long as they are biocompatible, sufficiently flexible to function as a catheter and sufficiently durable so that the catheter material is not breached during normal use.

Guidewire lumen 12 is preferably generally straight as shown in FIG. 1 and consists of a hollow tubular member defining a tubular channel 27 having a central axis 28. Guidewire lumen 12 is provided with a proximal opening 22 at the proximal end 16 of dual lumen catheter 10 and a distal opening 24 at the distal end 18 of dual lumen catheter 10. Proximal opening 22 of guidewire lumen 12 may be sealed from the environment using conventional means such as a Touhy Borst valve. The proximal opening 22 may be connected to other devices via a luer lock 26 in a manner whereby the catheter guidewire 38, shown in FIGS. 3–4, may be inserted through guidewire lumen 12 and pass through the luer lock 26 and out of the proximal end 16.

Dual lumen catheter 10 also includes a blind lumen 14 which consists of a generally tubular hollow member defining a tubular channel 31 having a central axis 29. Blind lumen 14 runs generally parallel to the guidewire lumen 12 for most of the length of dual lumen catheter 10 as shown in FIG. 1. Blind lumen 14 is closed off at the distal end 18 of dual lumen catheter 10 as shown in FIGS. 1–2. Preferably, blind lumen 14 includes a tapered distal end 30 as shown to avoid having any sharp edges or contours on the blind lumen 14 while closing off the tapered distal end 30. Optionally, blind lumen 14 includes an opaque marker 32 located in or near the tapered distal end 30 in order to allow location and/or visualization of the position of tapered distal end 30 of blind lumen 14 in the body using conventional devices such as x-ray machines. Opaque marker 32 is preferably fabricated from lead or other conventional radiopaque materials.

At the proximal end 16 of dual lumen catheter 10, blind lumen 14 preferably diverges from guidewire lumen 12 by a bend 36 in blind lumen 14 as shown in the portion blind lumen 14 which is designed to remain outside the body. This bend 34 coupled with the extra length of blind lumen 14 relative to guidewire lumen 12 separates the ends the blind lumen 14 and guidewire lumen 12 such that either or both of blind lumen 14 or guidewire lumen 12 may be attached at the proximal end 16 of dual lumen catheter 10 to one or more conventional devices for insertion or feeding of apparatus through dual lumen catheter 10. One example of such a device is an after loader, not shown. At the proximal end 16 of dual lumen catheter 10, the blind lumen 14 may also be sealed from the environment using any conventional means such as Touhy Borst valve. The proximal opening 22 may be connected to other devices such as a luer lock 34 as shown in FIG. 1.

The proximal end 16 of blind lumen 14 may be attached directly to an after-loader, not shown, for insertion of a radiation source wire 50 or other devices through blind lumen 14. Also, proximal end 16 of blind lumen 14 may be attached directly to a conventional radiation source shielding device, not shown, such as a source shielding pig to thereby eliminate the need for medical personnel to handle the radiation source wire 50 during a treatment procedure.

Referring now to FIG. 3, there is shown a longitudinal cross-sectional view of the dual lumen catheter 10 of the present invention without the disposable sheath 20. The Dual lumen catheter 10 is depicted with the guidewire 38 inserted into the tubular channel 27 of guidewire lumen 12 and the radiation source wire 50, shown schematically, inserted into the tubular channel 31 of blind lumen 14. As can be seen from FIG. 3, guidewire 38 traverses the entire length of guidewire lumen 12 and extends out of the distal end 18 of dual lumen catheter 10 through the distal opening 24 in guidewire lumen 12. Radiation source wire 50 is preferably inserted into blind lumen 14 until the distal end 52 is positioned in close proximity to the tapered portion 30 and the opaque marker 32 of the blind lumen 14 as shown in FIG. 3.

Referring now to FIG. 4, there is shown a frontal plane cross-section of a dual lumen catheter 10 including the disposable sheath 20. Shown in FIG. 4 is a preferred embodiment of the dual lumen catheter 10 of the present invention wherein the guidewire lumen 12 and the blind lumen 14 are formed integrally with one another such that guidewire lumen 12 shares a section 40 with blind lumen 14. In this manner, the dual lumen catheter 10 can be fabricated as a single part by, for example, an extrusion process, thereby eliminating the need to assemble and/or position two or more parts together to obtain the proper spatial relationship between the guidewire and blind lumens 12, 14.

FIG. 5 shows one embodiment of a radiation source wire 50 in accordance with the present invention. The radiation source wire 50 includes a wire core 52 which extends the entire length of radiation source wire 50. This wire core 52 is used to help maneuver the radiation source wire 50 through the tortuous body vessels to the treatment site via a catheter system such as that shown and described above. Typically, wire core 52 will have a length of at least 100 cm and it may be significantly longer.

Selecting the size of the outside diameter of the radiation source wire 50 requires a balance between the amount of trauma caused to body tissue through which the catheter system must pass in order to permit introduction of the radiation source wire 50 against the tensile strength and flexibility of the radiation source wire 50. Generally, the outside diameter of the radiation source wire 50 should not exceed about 0.075 cm and, more preferably, the outside diameter is about 0.02–0.05 cm in order to minimize trauma to body tissue. The diameter of the radiation source wire 50 may be adjusted to larger or smaller diameters to adjust the position of the radiation dose for larger or smaller body vessels.

The wire core 52 can be made of a variety of different materials. Particularly suitable materials are stainless steel, nickel/titanium alloys such as Nitinol® manufactured by Shape Memory Alloys, Sunnyvale, Calif., and polyimides. Suitable nickel/titanium alloys generally comprises from about 40–60% nickel, based on the total weight of the alloy, with the remainder being titanium.

An important feature of the wire core 52 of the radiation source wire 50 of the present invention is that the wire core is tapered at its distal end as shown in FIG. 5 where the tapering begins at the tapered section 54 of the wire core 52. The tapering of the wire core 52 results in a significant reduction in the outside diameter of wire core 52. For, example, the proximal end 56 of wire core 52 may have an outside diameter of about 0.01–0.075 whereas the distal end 58 of wire core 52 may have an outside diameter of about 0.01–0.04 cm as a result of tapered section 54. More preferably, the taper results in an outside diameter of the wire core 52 of about 0.015–0.035 cm.

Tapered wire core 52 is preferably fabricated by first preparing a wire of uniform outside diameter and then drawing the distal end 58 of the wire using conventional drawing processes to substantially uniformly reduce the diameter of the wire core 52 at the distal end 58. This provides a wire core 52 which is fabricated as a single unit and therefore does not contain any weaknesses due to the need to assemble several parts together. Such a wire core 52 minimizes the chance that a portion of the reduced diameter section of the wire core 52 will break off during use of the radiation source wire 50. The second advantage of the reduced diameter distal end 58 of wire core 52 is that it permits the application of additional materials to the outer surface of wire core 52 at distal end 58 while remaining within the maximum outside diameter range of up to about 0.075 cm. Also the tapered distal end 58 of wire core 52 is more flexible than would be a wire core 52 of larger diameter thereby rendering wire core 52 more suitable for negotiating twists and turns in body vessels.

In the preferred embodiment of the invention shown in FIGS. 5–6, the distal end 58 of wire core 52 includes a tube 60 applied over and around the outer surface of wire core 52. Tube 60 may be made from any material suitable for application of metal coatings thereon. A particularly preferred tube 60 is a single polyimide capillary tube which fits snugly over the outer surface of wire core 52. It is also possible to apply tube 60 as a coating on the surface of wire core 52. Preferably, the tube 60 is very thin thereby resulting in only a small increase in the outside diameter of the distal end 58 of the radiation source wire 50. For example, the outside diameter of the tube 60 may range from about 0.01–0.075 cm and more preferably from about 0.015–0.035 cm. Tube 60 is preferably affixed to the wire core 52 in any suitable manner such as using adhesive, by coating the material of tube 60 onto the surface of wire core 52 or by friction fit of tube 60 onto wire core 52, for example.

A base coating 62 is located on the outer surface of tube 60. Base coating 62 is optional though it is preferred to apply a base coating 62 to ensure good adherence of the radioactive material 64 to the outer surface of the tube 60. Thus, suitable base coatings 62 must provide good adherence to the tube 60 and also form a suitable substrate for application of the radioactive material 64. One example of a preferred material for base coating 62 is gold.

Onto the base coating 62 are applied radiopaque marker bands 66 which may be made from any suitable radiopaque material. The radiopaque marker bands 66 demarcate the boundaries of the radioactive material 64. Preferably, once the radiopaque marker bands 66 are applied, areas of the outer surface of the tube 60 which are not to include radioactive material 64, are masked with a masking material 68 such as polyester. Masking material 68 is applied to the outer surface of the radiopaque marker bands 66 as well as to the outer surface of the portion of the tube 60 which is not located between the two radiopaque marker bands 66 in order to prevent coating of radioactive material 64 onto the areas provided with masking material 68.

The next step in the fabrication of the radiation source wire 50 is to apply the radioactive material 64 atop the base coating 62 in the area between the radiopaque markers 66 by any suitable method for adhering the radioactive material 64 to the base coating 62. Suitable methods for application of radioactive material 64 to base coating 62 are described below. Any suitable radioactive material 64 may be employed but palladium-103 is the preferred radioactive material 64 for the radiation source wire 50 of the invention.

Finally, an optional sealing layer 70 may be applied at least over the radioactive material 64 to provide a sealed source which may be necessary to comply with certain government regulations which may require use of a sealed source for various reasons. Any conventional sealing layer 70 may be employed and preferred sealing layers are polymeric materials known to persons skilled in the art. Exemplary materials are polyimide, polyethylene, radiation stabilized polyolefins, radiation stabilized polyesters, but other similar materials can also be employed.

FIGS. 10 and 11 show another embodiment of the distal end of the radiation source wire of the present invention. The distal end 116 of wire core 106 includes a base coating 108 applied over and around the outer surface of wire core 106. Preferably, base coating 108 is a thin gold layer, which forms a suitable substrate for application of the radioactive material 100. Preferably, base coating 108 is formed on wire core 106 by direct vacuum deposition onto wire core 106. Preferably, the thickness of base coating 108 is less than 0.001 cm. More preferably, the thickness of base coating 108 is less than 0.0001 cm. Most preferably, the thickness of base coating 108 is less than 0.00001 cm.

Onto the base coating 108 are applied radiopaque marker bands 114 which may be made from any suitable radiopaque material The radiopaque marker bands 114 demarcate the boundaries of the radioactive material 100. Preferably, once the radiopaque marker bands 114 are applied, areas of the outer surface of the base coating 108 which are not to include radioactive material 100, are masked with a masking material 122 such as polyester. Masking material 122 is applied to the outer surface of the radiopaque marker bands 114 as well as to the outer surface of the portion of the base coating 108 which is not located between the two radiopaque marker bands 114 in order to prevent coating of radioactive material 100 onto the areas provided with masking material 122.

The next step in the fabrication of the radiation source wire 50 is to apply the radioactive material 100 atop the basing coating 108 in the area between the radiopaque markers 114 by any suitable method for adhering the radioactive material 100 to the base coating 108. Suitable methods for application of radioactive material 100 to base coating 108 are described below. Any suitable radioactive material 100 may be employed but palladium-103 is the preferred radioactive material 100 for the radiation source wire 50 of the invention.

The radioactive material 100 is then covered with a sealing layer 110. Any conventional sealing layer 110 may be employed and preferred sealing layers are polymeric materials known to persons skilled in the art. Exemplary materials are polyimide, polyethylene, radiation stabilized polyolefins, radiation stabilized polyesters, but other similar materials can also be employed. Preferably, sealing layer 110 is made from polyimide.

Then the sealing layer 110 is further covered with a tube 102 with a suitable inner diameter and wall thickness. The suitable inner diameter of the tube 102 is such that the tube fits over the wire core 106 covered with the sealing layer 110 loosely. At same time, the outer diameter of the tube 102 is small enough to minimize trauma during insertion into the vessels of a patient. Any conventional tube 102 may be employed and preferred materials for tube 102 are polymeric materials known to persons skilled in the art. Exemplary materials are polyimide, polyethylene, radiation stabilized polyolefins, radiation stabilized polyesters, but other similar materials can also be employed. Preferably, tube 102 is made from polyimide.

The space between the tube 102 and the sealing layer 110 is filled with a filler 104. Preferably, the filler 104 is silicone type material. More preferably, the filler 104 is a type of polydimethylsiloxane. Most preferably, the filler 104 is vinyl terminated polydimethylsiloxane, which can be further cured if necessary. Therefore, as an extra precaution in case the radioactive material 100 disintegrates for whatever reason, the disintegrated radioactive material 100 will still be contained within the radiation source wire 50.

Another advantage of the radiation source wire 50 of the present invention is that it does not require a separate guidewire for insertion and removal from the patient. Use of a separate guidewire has the disadvantages that the guidewire will partially shield the radiation dose unless it is removed during the procedure. Removal and reinsertion of the guidewire to avoid this problem causes significant delays in the procedure which are undesirable. A further advantage of the radiation source wire 50 of the present invention is that the only materials between the patient and the radioactive material 64 or 100 are a sealing layer 70 or 110, respectively and, a catheter lumen and perhaps a catheter sheath, none of which are generally made from radiation shielding materials. Thus, the present invention substantially reduces or eliminates the radiation shielding problem suffered by many prior art devices.

A further advantage of the present invention is that since the radioactive material 64 or 100 is applied to the outer surface of tube 60 or 102, respectively and around the entire circumference of radiation source wire 50, it can be provided to the patient in a substantially uniform shape which will provide a substantially uniform dose distribution. Further, the configuration of the present radiation source wire 50 permits centering of the radioactive material 64 or 100 by centering the radiation source wire 50 in a catheter lumen. Thus, if centering of the radioactive material 64 is desired for a particular procedure, it can be accomplished using the device of the present invention.

In alternative embodiments of the invention, it is possible to leave off sealing layer 70 or 110 if a sealed source is not required. Also, the radioactive material 64 or 100 can be applied directly to the wire core 52 or 106, respectively, if desired and thus the base coating 62 or 108 can be left off in some embodiments. For purposes of adhesion, if necessary, an intermediary layer such as gold may be applied directly to the wire core 52 or 106 to enhance the adhesion of the radioactive material 64 or 100 to the wire core 52 or 106, respectively. Also, the masking material 68 or 122 need not be employed if other conventional means of locating the radioactive material 64 or 100 at a particular location on tube 60 or 102, respectively are employed or it is desirable to coat the entire length of tube 60 or 102 with radioactive material. Also, it is possible to form the radiopaque marker bands 66 or 114 integrally with the tube 60 or 102, respectively. Additionally, a platinum core may be welded to the end of the wire core 52 or 106 to provide a substrate for coating the radioactive material and to act as the radiopaque marker 66 or 114. It is also possible to hollow out the distal end 58 or 116 of the wire core 52 or 106, place the radioactive material 64 or 100 in the wire core 52 or 106 and seal the hollowed out portion wire core 52 or 106, respectively.

A polymeric tube 60 or 102 can be attached to or inserted over the distal end 58 or 116 of the wire core 52 or 106 and the radioactive material 64 or 100 can be coated on or included in the polymeric tube 60 or 102. Also, the entire radiation source wire 50 may be enclosed in a polymeric protective sleeve, not shown, which may extend substantially the length of the radiation source wire 50.

The flexibility of the distal end 58 or 116 of the radiation source wire 50 can be selectively influenced by the application of different thicknesses of, for example the tube 60 or 102, base coating 62 or 108 or sealing layer 70 or 110, or by selecting different materials for one or more of these parts which have different degrees of flexibility. In this manner, the flexibility of the distal end 58 or 116 of radiation source wire 50 can be customized to some extent.

Optionally, the radiation source wire 50 may be provided with a variety of depth bands 72 located at different points along the proximal end 56 of radiation source wire 50. Depth bands 72 can be employed to determine the length of radiation source wire 50 which has been inserted into the patient through the catheter. Each Depth band 72 is preferably labeled with the length of the radiation source wire 50 from the distal tip 59 to the depth band 72. The distal tip 59 of the radiation source wire 50 may also be rounded to ease insertion and navigation through the lumen of a catheter.

Radiation source wire 50 may optionally include a retractable sheath, not shown, over the distal end 58 to shield the patient from radiation during insertion and removal of the radiation source wire 50. During treatment, the sheath is retracted to permit the radiation to be applied to the treatment area.

Radiation source wire 50 may be employed with the catheter system 10 of the present invention shown and described above or it may be employed with any suitable catheter system for insertion of a wire into a patient for treatment.

In another embodiment, the radiation source wire 50 may be provided in the form of a flexible polymer fiber or strand coated with radioactive material. A polymer is selected as the fiber or strand material which exhibits relatively low radiation shielding and good radiation stability, as well as having the flexibility and strain properties required to navigate the tortuous vessels of a patient.

As the radioactive material, it is possible to employ an isotopically engineered source designed to deliver an appropriate therapeutic dose of radiation over a predetermined treatment area and treatment time. The radioactive material may be engineered to have a specific isotopic composition of materials for the purpose of adjusting the level of activity, and, optionally, to reduce trace elements which may produce undesirable radiation. Also, two or more different radioactive isotopes can be engineered into a single source, if desired. Radioactive material can be made from isotopes which may be activated in a reactor to provide the desired level of radioactivity for treatment. Such a source can be activated for use and then decayed to a low level of radioactivity for reuse.

The radioactive material may be any suitable radioactive material known for use in therapeutic treatment of the human or animal body. Preferred radioactive materials 64 are gamma and/or beta-emitting sources. Examples of suitable radioactive materials 64 are Iodine-125, palladium-103, strontium-90, ruthenium-106, phosphorus-32, samarium-145, iridium-192, cobalt-60, radioactive vanadium-48 and yttrium-90. The radioactive material may be selected based on the specific needs of the particular treatment process, the half-life, the amount of radiation required and other parameters.

The radioactive material preferably comprises palladium-103 ("Pd-103"), and more preferably comprises carrier-free Pd-103, although even in preferred embodiments, mixtures of carrier-free Pd-103 and reactor grade Pd-103 may also be employed in some applications. Reactor grade Pd-103 may also be employed without carrier-free palladium-103 in some applications.

Reactor grade Pd-103 may be prepared in any suitable conventional manner such as by activation of palladium metal or by fabrication in a nuclear reactor. One disadvantage of reactor grade Pd-103 is that it may contain other undesirable radioactive palladium isotopes such as Pd-109 which emit potentially harmful types of radiation. Reactor grade Pd-103 can be fabricated to minimize such impurities. Nevertheless, in some applications, particularly those where irradiation will occur close to a vital internal organ, it may be desirable to avoid use of reactor grade Pd-103 for this reason. Moreover, the activity of reactor grade Pd-103 is relatively low.

Carrier-free Pd-103, on the other hand, can be made as a highly pure material, which contains essentially no undesirable radioactive isotopes of palladium. Moreover, carrier-free Pd-103 can be made having extremely high activities relative to reactor grade Pd-103 thereby providing greater flexibility in adjusting the specific activity of the radiation delivery device and permitting the use of smaller quantities of the expensive palladium material to achieve the same level of radiation dose. In accordance with the present invention, carrier-free Pd-103 can preferably be prepared in a particle accelerator.

Optionally, the radioactive material can further include a diluent. The diluent can be added to the radioactive material after it is eluted off the final purification anion exchange column. Alternatively, the diluent can be added during or prior to a purification process, if the diluent properties so allow. Suitable diluents for radioactive materials 64 may include platinum metal, palladium metal, rhodium metal, one or more of the various substrate materials listed above, or any other suitable material which is compatible with the radiation released by the radioactive material. More preferred diluents are biocompatible materials. Preferred diluents for carrier-free palladium are rhodium and palladium metals, usually in the form of a soluble metal salt such as $PdCl_2$. Because palladium metal will have the same affinity for an anion exchange column as the Pd-103, it can be added as a diluent prior to a purification step employing an anion exchange column and can be copurified along with the radioactive Pd-103.

Other preferred diluents for the various radioactive materials are certain polymeric materials which can be employed by, for example, homogeneously mixing the radioactive material with the polymer prior to its application to the substrate, or even by carrying out such mixing and using the mixture of polymeric material and radioactive material as the substrate itself.

Although the diluent may normally be considered an undesirable additive in a low energy emitting radiation source due to self-shielding effects, its addition in accordance with the present invention has been found to be advantageous in several respects which, in some applications, may make use of such a diluent desirable. Foremost, the added diluent can serve to promote strong adhesion of the radiation source material to the substrate, thereby forming a physiologically inert layer which will not allow the radioactive source to be mobilized into the circulation of a patient being treated.

Secondly, the addition of diluent provides the ability to adjust the specific activity of the radiation delivery device. This adjustment can be employed to provide an accurately determined desired level of therapeutic or apparent activity, as well as to compensate for the self-shielding effects of the diluent. Thirdly, if purification of the radioactive material is necessary, the presence of the diluent can, in some instances, reduce the loss of radioactive material 64 occurring during the purification process.

The amount of diluent added, therefore, will vary depending principally upon the amount of radioactive material. Preferably, from about 0.01 mg. to about 500 mg. of diluent per mCi of radioactive material can be used. Such amounts of diluent can ensure uniformity of the radioactive material 64 in the radiation delivery device and can promote adherence of the radioactive material 64 to the substrate.

If design considerations, e.g., the desired mass or therapeutic activity of the delivery device, so allow, nuclear reactor produced radioactive material can be added as a diluent to carrier-free radioactive source material and vice versa. Such addition may be employed, for example, to adjust the therapeutic activity of the radiation delivery device or to reduce the overall cost.

In an alternative embodiment, the wire core 52, 106 can be a thin fiber formed from a polymeric material. The polymeric material is preferably be selected from the group consisting of polyvinyl chloride, polysulfones, polyurethanes, polyamides, polyolefins, polyimides, cellulose esters, nylon, polyesters and modified or derivatized versions of one or more of these polymers. The skilled person is aware of the types of polymeric materials which are and radiation stable which can be employed herein.

Radiation can cause degradation of certain polymeric materials, as is known in the art. Particularly preferred polymeric materials for forming the substrate are polymeric materials which are resistant to such degradation due to exposure to radiation, such as the radiation stabilized polypropylene materials disclosed in U.S. Pat. Nos. 5,122, 593 and 5,140,073, the disclosures of which patents are hereby incorporated by reference to the extent that they relate to radiation stabilized polymeric materials suitable for use as substrates in the present invention.

Optionally, the polymeric materials forming the substrate can include one or more additives to enhance the adherence of the radiation source material to the substrate. Examples of such additives include absorbent materials such as activated carbon powder, activated charcoal, and ion exchange resins. Suitable ion exchange resins include sulfonated polystyrene resins, methylene-sulfonic phenolic resins, phosphoric polystyrene resins, polystyrene resins containing quaternary ammonium groups, pyridinium polystyrene resins, epoxy-polyamine resins containing tertiary and quaternary ammonium groups, iminodiacetic polystyrene resins, acrylic resins and polystyrene resins containing polyamine groups. Skilled persons are familiar with other additives which may be employed in the polymeric substrate for various reasons or specific applications.

The radioactive material may be applied by any suitable method for bonding the radioactive material to the substrate. Suitable processes include electroplating, chemical vapor deposition and electroless plating. Suitable coating materials for promoting electroplating, chemical vapor deposition or electroless plating onto a substrate are known to those of skill in the relevant art. Particularly preferred methods for applying the radioactive material 64 onto the surface of the substrate include electroless plating, chemical vapor deposition ("CVD"), physical vapor deposition, ion implantation and sputtering. In some embodiments it may also be desirable to apply the radiation source material to electroconductive substrates via electroplating.

Electroless plating of radioactive source material onto a substrate has the to advantage that it the process is applicable to a wide variety of substrates including non-conductive substrates. The process of the invention involves a first step cleaning the substrate surface to which the plating will be applied. Conventional cleaning processes can be employed such as ultrasound, rinsing with solvents and/or water, and other known surface cleaning processes. Once cleaned, the surface of the substrate is pretreated with, for example, $SnCl_2$ or $PdCl_2$. The stannous ions on the surface which result from this pretreatment process serve to attract palladium ions.

For electroless plating of Pd-102 (a precursor for making radioactive Pd-103 in situ) or Pd-103, the pretreated substrate is then activated with, for example, a $PdCl_2$/HCl solution. The stannous ions cause the $Pd^{2+}$ ions from $PdCl_2$ to reduce to $Pd^0$ and to adhere to the substrate. These $Pd^0$ sites form a catalytic surface on the substrate to enhance the deposition of Pd-102 or radioactive Pd-103 onto the substrate in a subsequent plating step. Other, similar metals, such as platinum group metals, may also be used in this step instead of palladium.

The Pd-102 or radioactive Pd-103 can then be deposited on the activated substrate by submerging the substrate in a heated solution of enriched Pd-102 or radioactive Pd-103. Once the deposition reaction subsides, the substrate plated with Pd-102 or radioactive Pd-103 is then dried and cooled.

The electroless plating process has the additional advantages that there is very little loss of expensive palladium during the process and that a substantially uniform coating can be applied to a substrate in a relatively short time period. Also, the electroless plating process can be employed to provide a conductive coating on a non-conductive substrate to prepare the substrate for subsequent electroplating of the radioactive materials thereon.

Processes for electroplating Pd-103 onto various electro-conductive substrates are known to persons skilled in the art from U.S. Pat. No. 5,405,309, the disclosure of which is incorporated by reference for the purpose of describing the details of a suitable electroplating process for Pd-103. For other radioactive source materials, similar electroplating processes can be used. Also, in many cases if there is sufficient mass of the radioactive source material available, conventional electroplating processes may be suitable for application of the radioactive source to the substrate.

Alternatively, the radiation source material can be uniformly mixed with a diluent and then coated onto the outer surface of the substrate. Preferably, the radiation source material is dissolved in the diluent although it may also be in the form of a particle suspension, if desired. Suitable diluents for this purpose include those described above as well as the substrate materials described above which may be used in polymer masterbatching processes, for example. Preferred diluents are adhesives and polymeric materials such as, for example, urethanes, acrylics, chloroprenes, polyvinyl alcohols, polyvinyl chorides, nylons, or the like.

The radioactive material can be supplied to above-described incorporation processes as a solid or in solution, as may be appropriate for the particular incorporation process. If supplied as a solid, the radiation source material can be a powder, or a mixture of radioactive source material and a suitable solid diluent. Alternatively, the radiation source material may be supplied as solid reactor grade radioactive source material or as a solid form of a precursor of the radioactive source which may later be activated in situ, after application of the precursor to the substrate of the radiation delivery device.

If supplied as a solution, the radiation source material can be, for example, a palladium amine complex obtained directly from a purification process. Alternatively, the radioactive source can be dissolved in an appropriate solvent to obtain a desired solution for a particular incorporation process. Suitable solvents for these materials are known in the art.

Referring to FIG. 8, there is shown a cross-sectional view of a source train cask 80 which may be employed with one or both of the catheter system 10 and radiation source wire 50 of the present invention to store and feed the radioactive source wire 50 to the catheter system 10. Source train cask 80 is formed from a housing 82 which is may be a radiation shielding material but need not be. Housing 82 is provided with a base 84 for standing the source train cask 80 stably on a flat surface for use.

Housing 82 of source train cask 80 can be opened by, for example, removing one end, to permit introduction of an internal pig 86 into source train cask 80. Source train cask 80 also includes a means 88 for affixing internal pig 86 into position in source train cask 80 to align the annular bore 90 of internal pig 86 with openings 92 in the housing 82 of source train cask 80 as shown in FIG. 8. Openings 92 may be sealed from the environment by, for example luer locks 94.

In use, radiation source wire 50 is positioned within annular bore 90 of internal pig 86 with the radioactive material 64 located completely within internal pig 86. Internal pig 86 is then positioned and affixed within source train cask 80 as shown in FIG. 8 with the annular bore 90 aligned with openings 92 in housing 82 of source train cask 80. The proximal end 56 of the radiation source wire 50 is fed through a luer lock 94 as shown and a catheter sheath interface 96 is attached to the other opening 92 in housing 82. The source train cask 80 is then closed and positioned to be attached to the proximal end 16 of blind lumen 14 of the catheter system 10 for feeding the radiation source wire 50 into the blind lumen 14 to accomplish the treatment procedure. Optionally, a motorized after-loader, not shown, may be used in association with source train cask 80 to feed the radiation source wire 50 to the catheter system 10. In this manner, source train cask 80 protects medical personnel from exposure to radiation during the procedure.

Advantageously, internal pig 86 is a container within which the radioactive material 64 is shipped to the location of use thereby greatly simplifying the procedure by eliminating the need to directly handle the radioactive material 64. Internal pig 86 may optionally include a site glass 98 through which the radioactive material 64 can be viewed.

The foregoing embodiments of the invention have been presented for the purpose of illustration and description only and are not to be construed as limiting the scope of the invention in any way. The scope of the invention is to be determined from the claims appended hereto.

What is claimed is:

1. A radioactive source wire comprising:
    a unitary wire core formed from a single part and having a distal portion, a distal end, and a proximal portion, said unitary wire core extending a sufficient distance along said radioactive source wire to ensure that at least a portion of the unitary wire core extends outside a patient during use of the radioactive source wire,
    wherein the distal portion of the unitary wire core has a tapered section with a thickness that tapers from a first diameter at a distance from the distal end to a second, lesser diameter at the distal end of the unitary wire core,
    a sufficient amount of a radioactive material associated with the distal portion of the source wire to deliver a therapeutic dose of radiation to a human or animal patient, and
    a tube located on an outer surface of the wire core, a base coating on the outer surface of the tube, which promotes adherence of the radioactive material to the outer surface of the tube, and wherein the radioactive material is adhered to the outer surface of the tube.

2. A radioactive source wire as claimed in claim 1, wherein the base coating comprises gold.

3. A radioactive source wire as claimed in claim 1, further comprising a plurality of radiopaque marker bands applied to the base coating and wherein at least two of the radiopaque marker bands are located at distal and proximal boundaries of the radioactive material on said source wire.

4. A radioactive source wire as claimed in claim 3, wherein the radioactive material is distributed substantially uniformly about a circumference of the outer surface of the tube.

5. A radioactive source wire as claimed in claim 4, wherein said tube, base layer, radioactive material, radiopaque marker bands and said sealing layer are located on said tapered portion of said wire core in a manner whereby a diameter of the distal portion of the source wire does not exceed the first diameter of the wire core.

6. A radioactive source wire as claimed in claim 3, further comprising a sealing layer on an outer surface of the radioactive material.

7. A radioactive source wire as claimed in claim 6 wherein the radioactive material is adhered to the wire core and which further comprises a tube located around the wire core and the radioactive material, and a base layer on said wire core, which promotes adherence of the radioactive material to said wire core.

8. A radioactive source wire as claimed in claim 7, wherein said tube, base layer, radioactive material, radiopaque marker bands and said sealing layer are located on said tapered portion of said wire core in a manner whereby a diameter of the distal portion of the source wire does not exceed the first diameter of the wire core.

9. A radioactive source wire as claimed in claim 6, wherein the radioactive material is adhered to the wire core and which further comprises a tube located around the wire core and the radioactive material, and a plurality of radiopaque marker bands applied to the base coating and wherein at least two of the radiopaque marker bands are located at distal and proximal boundaries of the radioactive material on said source wire.

10. A radioactive source wire as claimed in claim 9, wherein said radioactive material is distributed substantially uniformly about a circumference of said outer surface of said wire core.

11. A radioactive source wire as claimed in claim 1, wherein the tapered section of the distal portion of the wire core is formed by drawing the wire core.

12. A dual lumen catheter system for delivery of a radioactive source wire to a localized area of a human or animal body, said catheter system comprising:
- a guidewire lumen,
- a blind lumen, and
- a radioactive source wire as claimed in claim 6.

13. A dual lumen catheter system for delivery of a radioactive source wire to a localized area of a human or animal body, said catheter system comprising:
- a guidewire lumen,
- a blind lumen, and
- a radioactive source wire as claimed in claim 9.

14. A radioactive source wire comprising:
- a wire core having a distal portion, a distal end, and a proximal portion,
- wherein the distal portion of the wire core has a tapered section with a thickness that tapers from a first diameter at a distance from the distal end to a second, lesser diameter at the distal end of the wire core,
- a sufficient amount of a radioactive material adhered to at least a portion of the tapered section of the distal portion of the wire core to deliver a therapeutic dose of radiation to a human or animal patient,
- a tube located around the wire core and the radioactive material, and
- a base layer on at least a portion of the tapered section of the distal portion of the wire core, and wherein the radioactive material is adhered to the wire core by the base layer.

15. A radioactive source wire as claimed in claim 14, further comprising a plurality of radiopaque marker bands applied to the base layer, and wherein at least two of the radiopaque marker bands are located at distal and proximal boundaries of the radioactive material.

16. A radioactive source wire as claimed in claim 15, wherein said radioactive material is distributed substantially uniformly about a circumference of said outer surface of said wire core.

17. A radioactive source wire as claimed in claim 16, further comprising a sealing layer on an outer surface of the radioactive material.

18. A radioactive source wire as claimed in claim 17, wherein said radioactive material, said tube, said base layer, said radiopaque marker bands and said sealing layer are located on said tapered portion of said wire core in a manner whereby a diameter of the distal portion of the source wire does not exceed the first diameter of the wire core.

19. A dual lumen catheter system for delivery of a radioactive source wire to a localized area of a human or animal body, said catheter system comprising:
- a guidewire lumen,
- a blind lumen, and
- a radioactive source wire as claimed in claim 1.

20. A dual lumen catheter system for delivery of a radioactive source wire to a localized area of a human body, said catheter system comprising:
- a guidewire lumen,
- a blind lumen, and
- a radioactive source wire as claimed in claim 7.

21. A dual lumen catheter system for delivery of a radioactive source wire to a localized area of a human or animal body, said catheter system comprising:
- a guidewire lumen,
- a blind lumen, and
- a radioactive source wire as claimed in claim 14.

* * * * *